United States Patent [19]

Aoyama et al.

[11] Patent Number: 5,773,404
[45] Date of Patent: Jun. 30, 1998

[54] AZEOTROPIC COMPOSITION

[75] Inventors: Hirokazu Aoyama; Satoshi Ide; Akinori Yamamoto, all of Settsu, Japan

[73] Assignee: Daikin Industries, Ltd., Osaka, Japan

[21] Appl. No.: 722,023

[22] PCT Filed: Apr. 10, 1995

[86] PCT No.: PCT/JP95/00705

§ 371 Date: Oct. 11, 1996

§ 102(e) Date: Oct. 11, 1996

[87] PCT Pub. No.: WO95/28373

PCT Pub. Date: Oct. 26, 1995

[30] Foreign Application Priority Data

Apr. 13, 1994 [JP] Japan ..................... 6-075124

[51] Int. Cl.$^6$ ............ C11D 17/00; C07C 23/06
[52] U.S. Cl. ............ 510/415; 570/123; 521/137
[58] Field of Search .......... 510/415; 570/123; 521/137

[56] References Cited

U.S. PATENT DOCUMENTS 3,850,759 11/1974 Hutchinson ............... 203/58
5,599,783 2/1997 Ide et al. ................. 510/412

FOREIGN PATENT DOCUMENTS

| 60-63269 | 4/1985 | Japan . |
| 5-78652 | 3/1993 | Japan . |
| 5-179039 | 7/1993 | Japan . |
| 5-295157 | 11/1993 | Japan . |
| 5-331489 | 12/1993 | Japan . |

OTHER PUBLICATIONS

Michael Van Der Puy, *Journal of Fluorine Chemistry*, Estimation of Hydrocarbon Solubilities in Hydrofluorocarbons 67 (1994), pp. 215–224.

*Primary Examiner*—C. Warren Ivy
*Assistant Examiner*—Lymon H. Smith
*Attorney, Agent, or Firm*—Armstrong, Westerman, Hattori, McLeland & Naughton

[57] ABSTRACT

To provide an azeotropic composition comprising cis-1,1,2,2,3,4-hexafluorocyclobutane and at least one compound selected from the group consisting of methanol, ethanol, isopropanol, n-propanol, tert-butanol, cyclopentane, n-octane, isooctane, n-heptane and methylcyclohexane, and a detergent, drying agent and foaming agent, which use the above-mentioned azeotropic composition. The azeotropic composition of the present invention is an alternative fleon composition having less influence on plastics, being excellent in solvency and having less influence on the ozone layer.

24 Claims, No Drawings

AZEOTROPIC COMPOSITION

TECHNICAL FIELD

The present invention relates to an azeotropic composition comprising cis-1,1,2,2,3,4-hexafluorocyclobutane (hereinafter referred to as "HFC-C336ee") and a specific alcohol and/or a specific hydrocarbon compound.

BACKGROUND ART

Trichlorotrifluoroethane (hereinafter referred to as "CFC-113") which is a chlorofluoroethane compound has been used widely as a solvent, detergent and the like solely or in the form of mixture or azeotropic composition with other organic solvent(s), because it is non-flammable and biologically less toxic and in addition, is excellent in selective solvency to oil and fat, grease, wax and the like without attacking high molecular substances such as plastics and rubbers.

In recent years, there has been raised a problem of environmental pollution on world-wide scale, that is, depletion of the ozone layer surrounding the earth due to chlorofluoroethane compounds (hereinafter referred to as "perhaloethane") such as CFC-113 in which all of hydrogen are replaced by chlorine and fluorine, and the chlorofluoroethane compounds cannot be used wholly in 1995. Also there is the same problem with respect to hydrochlorofluorocarbons (HCFC) used as alternatives for the perhaloethane, and prohibition of use thereof is slated in 2020.

It has been proposed to use hydrofluorocarbon (HFC) instead of CFC and HCFC. For example, there are 1,1,2,2,3,3,4,4,-octafluorobutane (HFC-338pcc), 1,1,1,2,3,4,4,5,5,5-decafluoropentane (HFC43-10mee), HFC-C336 and the like. JP-A-213397/1992 describes an azeotropic composition comprising HFC-C338pcc and methanol used as a detergent. Also U.S. Pat. No. 5,064,559 describes an azeotropic composition comprising HFC43-10mee and an alcohol used as a detergent. With respect to HFC-C336, there have been proposed single use thereof as a foaming agent or a detergent (JP-A-295157/1993 and JP-A-331489/1993).

However, HFC-338pcc and HFC43-10mee are not sufficient in solvency against contaminants such as metal processing oil, oil and fat, grease, wax and rosin flux, and are expensive because their syntheses are very difficult. Furthermore, with respect to HFC-C336, there are many isomers having different characteristics, and it is difficult to find out, from them, a compound having excellent properties. Similarly to the above-mentioned compounds, HFC-C336 itself has no sufficient solvency against oil and fat, flux and the like.

Solvency and flammability of a solvent can be adjusted by adding a co-solvent, that is to say, by preparing a mixed solvent. However, even if a mixed solvent is simply prepared, one component is condensed due to vaporization, which causes inconveniences such as change of the solvency and exhibition of flammability.

It is known that an azeotropic mixture is useful since it is vaporized/condensed at a specified temperature and composition. If a solvent mixture is not azeotropic, it is not preferred in practical use because its volatile component having a low boiling point is first vaporized to change its composition, thereby lowering solvency and increasing flammability.

Also the azeotropic composition is preferred in vapor-cleaning process including re-distilling step, final rinsing step and drying step. If the composition is not azeotropic, one component thereof is condensed in the re-distillation step, and thus safety and efficiency in the vapor-cleaning process are impaired.

Heretofore, there have been found many azeotropic compositions of fluorocarbons, and some of them have been used as a vapor-cleaning agent, a degreasing agent or a flux removing agent. However, it is difficult to expect whether or not an azeotropic composition can be formed, and therefore, an effort to find a novel azeotropic system applicable to this field has been continued.

An object of the present invention is to provide an azeotropic composition having increased solvency and non-flammability without using CFC and HCFC and being less detrimental to the ozone layer.

DISCLOSURE OF THE INVENTION

The present invention relates to an azeotropic composition comprising HFC-C336ee and at least one compound selected from the group consisting of methanol, ethanol, isopropanol, n-propanol, tert-butanol, cyclopentane, n-octane, isooctane, n-heptane and methylcyclohexane.

The present invention also relates to a cleaning composition comprising the above-mentioned azeotropic composition, and to a method of cleaning surfaces of solid articles with the cleaning composition.

The present invention further relates to a foaming agent comprising the above-mentioned azeotropic composition, and to a method of producing foamed resin articles by using the foaming agent.

BEST MODE FOR CARRYING OUT THE INVENTION

HFC-C336ee used in the present invention is a known compound (J. Chem. Soc. 3198 (1961)) having a boiling point of 64.5° C.

The compound forming an azeotropic composition with HFC-C336ee is an alcohol of methanol, ethanol, isopropanol, n-propanol and tert-butanol and a hydrocarbon of cyclopentane, n-octane, isooctane, n-heptane and methylcyclohexane. The azeotropic composition containing the alcohol has a high solvency particularly for rosin flux, and an increased degreasing power for oil and fat, grease, wax and the like and dewatering ability. The azeotropic composition containing the hydrocarbon has a high solvency for oil and fat, grease, wax and the like, and in addition, enhanced compatibility with other organic solvents and surfactants, for instance, industrial gasoline, higher alcohols and ethers. In an azeotropic composition of three components, i.e. HFC-C336ee, the alcohol and the hydrocarbon, the characteristic properties of each component work synergistically, and thus the solvency is enhanced.

Examples of the azeotropic composition are as follows:

(1) Two-component azeotropic composition (azeotropic temperature: 55.2° C.) comprising HFC-C336ee and methanol and having a weight ratio of 87 to 89/13 to 11 under atmospheric pressure (hereinafter the same).

(2) Two-component azeotropic composition (azeotropic temperature: 60.5° C.) comprising HFC-C336ee and ethanol and having a weight ratio of 91 to 94/9 to 6.

(3) Two-component azeotropic composition (azeotropic temperature: 62.5° C.) comprising HFC-C336ee and isopropanol and having a weight ratio of 91 to 94/9 to 6.

(4) Two-component azeotropic composition (azeotropic temperature: 64.2° C.) comprising HFC-C336ee and n-propanol and having a weight ratio of 96 to 98/4 to 2.

(5) Two-component azeotropic composition (azeotropic temperature: 63.9° C.) comprising HFC-C336ee and tert-butanol and having a weight ratio of 94 to 96/6 to 4.
(6) Two-component azeotropic composition (azeotropic temperature: 39.9° C.) comprising HFC-C336ee and cyclopentane and having a weight ratio of 55 to 65/45 to 35.
(7) Two-component azeotropic composition (azeotropic temperature: 63.5° C.) comprising HFC-C336ee and n-octane and having a weight ratio of 95 to 97/5 to 3.
(8) Two-component azeotropic composition (azeotropic temperature: 61.2° C.) comprising HFC-C336ee and isooctane and having a weight ratio of 85 to 89/15 to 11.
(9) Two-component azeotropic composition (azeotropic temperature: 60.3° C.) comprising HFC-C336ee and n-heptane and having a weight ratio of 85 to 90/15 to 10.
(10) Two-component azeotropic composition (azeotropic temperature: 60.5° C.) comprising HFC-C336ee and methylcyclohexane and having a weight ratio of 85 to 91/15 to 9.
(11) Three-component azeotropic composition (azeotropic temperature: 57.6° C.) comprising HFC-C336ee, ethanol and n-heptane and having a weight ratio of 78 to 84/6 to 8/10 to 14.
(12) Three-component azeotropic composition (azeotropic temperature: 63.4° C.) comprising HFC-C336ee, tert-butanol and n-octane and having a weight ratio of 93 to 97/1 to 3/2 to 4.

The composition of the present invention is the composition comprising HFC-C336ee, the specific alcohol and/or the specific hydrocarbon compound and having the characteristic properties as mentioned above, and in addition, is azeotropic, which makes easy the operation, recovery and re-use of the liquid and applicable to the vapor-cleaning process. Further, the composition exhibits great effects particularly on removal of metal processing oil, oil and fat and rosin flux, and as a foaming agent for foamed resin articles. Also the composition is chemically stable, is excellent in selective solvency which makes it possible to rinse and remove stains only almost without any influence on plastic, rubber and metal, and has a good drying ability of wet products. In addition, the composition has less influence on depletion of the ozone layer as compared with CFC and HCFC.

To the composition of the present invention may be added a stabilizer.

As properties of such a stabilizer, it is a matter of course that a large effect on stabilization of the composition is necessary, and it is preferable that the stabilizer is simultaneously distilled in the distillation process or forms azeotropic system.

Examples of the stabilizer are, for instance, an aliphatic nitro compound such as nitromethane, nitroethane or nitropropane; an acetylene alcohol such as 3-methyl-1-butyn-3-ol or 3-methyl-1-pentyn-3-ol; an epoxide such as glycidol, methylglycidyl ether, allylglycidyl ether, phenylglycidyl ether, 1,2-butylene oxide, cyclohexene oxide or epichlorohydrin; an ether such as dimethoxymethane, 1,2-dimethoxyethane, 1,4-dioxane or 1,3,5-trioxane; an unsaturated hydrocarbon such as hexene, heptene, octene, 2,4,4-trimethyl-1-pentene, pentadiene, octadiene, cyclohexene or cyclopentene; an olefinic alcohol such as allyl alcohol, 1-butene-3-ol or 3-methyl-1-butene-3-ol; an acrylate such as methyl acrylate, ethyl acrylate or butyl acrylate; and the like. These stabilizers may be used solely or in a mixture of two or more thereof. Among them, nitromethane is preferable. Also together with the above-mentioned stabilizers, there may be used phenols such as phenol, trimethylphenol, cyclohexylphenol, thymol, 2,6-di-t-butyl-4-methylphenol, butyl hydroxy anisol and isoeugenol, amines such as hexylamine, pentylamine, dipropylamine, diisopropylamine, diisobutylamine, triethylamine, tributylamine, pyridine, N-methylmorpholine, cyclohexylamine, 2,2,6,6-tetramethylpiperidine and N,N'-diallyl-p-phenylenediamine; triazoles such as benzotriazole, 2-(2'-hydroxy-5-methylphenyl)benzotriazole and chlorobenzotriazole and the like. By the combination use thereof, further excellent synergistic stabilizing effects can be exhibited.

An amount of the above-mentioned stabilizer varies depending on kind thereof, and there is no fixed amount, but usually it is preferable to use 0.1 to 5% by weight, more preferably 0.5 to 5% by weight on the basis of the composition of the present invention. In case where nitromethane is used, it is preferable to use about 0.1 to about 5.0% by weight. The stabilizer is used in an amount not impairing the azeotropic property. Since usually a small amount of stabilizer is added, the addition thereof does not affect greatly the azeotropic property.

The present invention further relates to the cleaning composition comprising the above-mentioned azeotropic composition, particularly the degreasing composition and flux removing composition, and also relates to the method of rinsing the surfaces of solid articles with that cleaning composition. The cleaning composition of the present invention exhibits its effect in removal of rosin fluxes, various fats and oils, greases, waxes, industrial gasolines, higher alcohols, ethers and the like. Also when the above-mentioned specific alcohol is employed as the azeotropic component, high solvency is exhibited against the rosin fluxes, and solvency against fats and oils, greases and waxes is increased. When the above-mentioned specific hydrocarbon is used as the azeotropic component, solvency against fats and oils, greases and waxes and in addition, other organic solvents and surfactants, for example, industrial gasolines, higher alcohols and ethers is enhanced.

The cleaning composition of the present invention has less influence on plastics.

The rinsing can be conducted by bringing the above-mentioned cleaning composition into contact with the surfaces of solid articles, for example, by dipping method, dipping method using ultrasonic wave, spray rinsing method, vapor cleaning method or a combined method thereof.

The present invention also relates to the drying agent for dewatering. The azeotropic compositions (1) to (5) containing the above-mentioned alcohols have high dewatering ability, and by using those compositions as the drying agent for dewatering, the surfaces of solid articles can be dried.

The present invention further relates to the foaming agent comprising the above-mentioned azeotropic composition and the method of producing the foamed resin articles by using the foaming agent.

The azeotropic composition of the present invention has an azeotropic point of 39.9° to 64.2° C. and is chemically stable, and therefore, is suitable as a foaming agent for producing the foamed resin articles. Examples of the foamed resin articles are polyurethane foam, polystyrene foam, polypropylene foam, polyethylene foam, phenol foam and the like. Among them, as the foaming agent for the polyurethane foam, there is suitably used the above (6), and for the polystyrene foam, polypropylene foam, polyethylene foam and phenol foam, the above (6) to (10) are suitable.

As the expansion method, there can be employed the same method as the conventional one using CFC, HCFC or an azeotropic composition containing them. For example, in case where the polyurethane foam is produced, the foamed resin articles can be obtained through usual method by allowing an active hydrogen compound having at least two active hydrogen-containing groups such as polyols to react with polyisocyanate compounds in the presence of a catalyst and the foaming agent of the present invention.

The present invention is then explained with examples, but is not limited to the examples.

EXAMPLES 1 TO 10

A 100 cc distillation flask was charged with 20 g of C336ee (boiling point: 64.5° C.) and 20 g of each second component shown in Table 1, to conduct distillation under atmospheric pressure by using a rectifying tube having 20 theoretical stages. Azeotropic property was observed at a boiling point as shown in Table 1, which is lower than that of the both liquids. The obtained distillate was analyzed through gas chromatography, and as a result, the proportion of C336ee and the second component in the distillate was as shown in Table 1.

using C336ee solely as for Comparative Example 1. The results are shown in Table 3.

TABLE 3

| Example | Azeotropic composition | Solvency (%) | Water removal (%) |
|---|---|---|---|
| 13 | Ex. 1 | 99.9 | 99 |
| 14 | Ex. 2 | 99.9 | 99 |
| 15 | Ex. 3 | 99.9 | 99 |
| 16 | Ex. 4 | 99.9 | 99 |
| 17 | Ex. 5 | 99.9 | 99 |
| 18 | Ex. 6 | 99.9 | 99 |
| 19 | Ex. 7 | 99.9 | 99 |
| 20 | Ex. 8 | 99.9 | 99 |
| 21 | Ex. 9 | 99.9 | 99 |
| 22 | Ex. 10 | 99.9 | 99 |
| 23 | Ex. 11 | 99.9 | 99 |
| 24 | Ex. 12 | 99.9 | 99 |
| Com. Ex. 1 | C336ee | 99.7 | 95 |

TABLE 1

| | Second component | Boiling point of second component (°C.) | Azeotropic point (°C.) | Proportion of distillate (% by weight) | |
|---|---|---|---|---|---|
| | | | | Second component | C336ee |
| Ex. 1 | Methanol | 64.6 | 55.2 | 12.5 | 87.5 |
| Ex. 2 | Ethanol | 78 | 60.5 | 8.4 | 91.6 |
| Ex. 3 | Isopropanol | 82.4 | 62.5 | 6.9 | 93.1 |
| Ex. 4 | n-Propanol | 94 | 64.2 | 2.4 | 97.6 |
| Ex. 5 | tert-Butanol | 83 | 63.9 | 5 | 95 |
| Ex. 6 | Cyclopentane | 50 | 39.9 | 41.4 | 58.6 |
| Ex. 7 | n-Octane | 126 | 63.5 | 4.3 | 95.7 |
| Ex. 8 | Isooctane | 98.5 | 61.2 | 13.7 | 86.3 |
| Ex. 9 | n-Heptane | 98 | 60.3 | 11.8 | 88.2 |
| Ex. 10 | Methylcyclohexane | 101 | 60.5 | 10.5 | 89.5 |

EXAMPLES 11 AND 12

A 100 cc distillation flask was charged with 20 g of C336ee (boiling point: 64.5° C.), 20 g of each second component and 20 g of each third component shown in Table 2, to conduct distillation under atmospheric pressure by using a rectifying tube having 20 theoretical stages. Azeotropic property was observed at a boiling point lower than that of each liquid as shown in Table 2. The obtained distillate was analyzed through gas chromatography, and as a result, the proportion of C336ee and each of the second and third components was as shown in Table 2.

(Degreasing ability)

A double-tank type bench cleaning machine having an ultrasonic tank and a vaporizing tank was charged with the azeotropic composition of the present invention to clean a 100-mesh cylindrical metal net (25φ×15 Hmm), to which metal processing oil (G6250, available from Nippon Kosakuyu Kabushiki Kaisha) adhered, and thus degreasing test was conducted. In the cleaning, ultrasonic wave cleaning was carried out for one minute, respectively in a heated bath having a temperature lower by about 5° C. than that of

TABLE 2

| | | | | Proportion of distillate (% by weight) | | |
|---|---|---|---|---|---|---|
| | Second component | Third component | Azeotropic point (°C.) | C336ee | Second component | Third component |
| Ex. 11 | Methanol | n-Heptane | 57.6 | 80.3 | 6.8 | 12.9 |
| Ex. 12 | tert-Butanol | n-Octane | 63.4 | 94.9 | 1.8 | 3.3 |

EXAMPLES 13 TO 24

The following tests were carried out by using the azeotropic compositions obtained in Examples 1 to 12 and by the azeotropic composition, and then vapor-cleaning was conducted for one minute, followed by measurement of an amount of oil remaining on the metal net with an oil concentration meter (available from Kabushiki Kaisha Horiba Seisakusho). The removal percentage of oil was determined as the solvency (%).

(Dewatering test)

A test piece made of iron (30×30×2t mm, a drilled hole of 7φ in the center) was dipped in water, and then dipped in the azeotropic composition of the present invention at room temperature for 30 seconds, followed by rinsing with a given amount of methanol anhydride. Water content in that rinsing liquid (methanol) was analyzed through Karl Fischer's method to obtain a water removal percentage (%).

EXAMPLES 25 TO 36

Various plastics shown in Table 4 were dipped in the azeotropic composition of the present invention obtained in Examples 1 to 12, at 25° C. for ten minutes. Immediately after being taken out, variation of weight of the plastics was measured and evaluated in accordance with the following criteria.
0: Almost no influence is seen (change in weight: 0 to 1%).
1: Slight swelling occurs, which is substantially no problem (change in weight: 1 to 5%).
2: Swelling occurs to deteriorate plastics (change in weight: not less than 5%)
The results are shown in Table 4.

TABLE 4

| Example | Azeotropic composition | ABS resin | Poly-carbonate | Acrylic resin | Epoxy resin | Poly-phenylene oxide |
|---|---|---|---|---|---|---|
| 25 | Ex. 1 | 0 | 0 | 1 | 0 | 0 |
| 26 | Ex. 2 | 0 | 0 | 1 | 0 | 0 |
| 27 | Ex. 3 | 0 | 0 | 1 | 0 | 0 |
| 28 | Ex. 4 | 0 | 0 | 1 | 0 | 0 |
| 29 | Ex. 5 | 0 | 0 | 1 | 0 | 0 |
| 30 | Ex. 6 | 0 | 0 | 1 | 0 | 0 |
| 31 | Ex. 7 | 0 | 0 | 1 | 0 | 0 |
| 32 | Ex. 8 | 0 | 0 | 1 | 0 | 0 |
| 33 | Ex. 9 | 0 | 0 | 1 | 0 | 0 |
| 34 | Ex. 10 | 0 | 0 | 1 | 0 | 0 |
| 35 | Ex. 11 | 0 | 0 | 1 | 0 | 0 |
| 36 | Ex. 12 | 0 | 0 | 1 | 0 | 0 |

EXAMPLES 37 TO 41

(Expansion test)

A mixture solution was prepared by premixing, with 100 g of polyol (polyether polyol having 470 of hydroxyl value and prepared by reacting polypropylene oxide with sucrose and ethylenediamine), 2 g of a silicone surfactant, 1 g of water, a necessary amount of N,N,N',N'-tetramethylhexane-1,6-diamine as a catalyst for obtaining a gel time of 60 seconds and a proper amount of the foaming agent (azeotropic compositions of Examples 6 to 10) of the present invention for endowing a foamed article with a core density of 30 kg/m³. The obtained mixture solution and 148 g of polymethylene polyphenyl isocyanate were mixed, and expanded to give a hard urethane foam. The results are shown in Table 5. Estimation was made by comparing with the case where CFC-11 was used as the foaming agent.

○: Not less than the same level as in CFC-11
Δ: Slightly inferior to CFC-11
X: Inferior to CFC-11

TABLE 5

| Ex. | Azeotropic composition | External appearance of foam | Compression strength | Heat conductivity |
|---|---|---|---|---|
| 37 | Ex. 6 | ○ | ○ | ○ |
| 38 | Ex. 7 | ○ | ○ | Δ |
| 39 | Ex. 8 | ○ | ○ | Δ |
| 40 | Ex. 9 | ○ | ○ | Δ |
| 41 | Ex. 10 | ○ | ○ | Δ |

INDUSTRIAL APPLICABILITY

The present invention can provide an azeotropic composition having less influence on the ozone layer and on plastics. The azeotropic composition of the present invention is useful as a detergent, drying agent and foaming agent.

We claim:
1. An azeotropic composition comprising cis-1,1,2,2,3,4-hexafluorocyclobutane and at least one compound selected from the group consisting of methanol, ethanol, isopropanol, n-propanol, tert-butanol, cyclopentane, n-octane, isooctane, n-heptane and methylcyclohexane.
2. The azeotropic composition of claim 1, which consists of cis-1,1,2,2,3,4-hexafluorocyclobutane and methanol in a weight ratio of 87 to 89/13 to 11 under atmospheric pressure.
3. The azeotropic composition of claim 1, which consists of cis-1,1,2,2,3,4-hexafluorocyclobutane and ethanol in a weight ratio of 91 to 94/9 to 6 under atmospheric pressure.
4. The azeotropic composition of claim 1, which consists of cis-1,1,2,2,3,4-hexafluorocyclobutane and isopropanol in a weight ratio of 91 to 94/9 to 6 under atmospheric pressure.
5. The azeotropic composition of claim 1, which consists of cis-1,1,2,2,3,4-hexafluorocyclobutane and n-propanol in a weight ratio of 96 to 98/4 to 2 under atmospheric pressure.
6. The azeotropic composition of claim 1, which consists of cis-1,1,2,2,3,4-hexafluorocyclobutane and tert-butanol in a weight ratio of 94 to 96/6 to 4 under atmospheric pressure.
7. The azeotropic composition of claim 1, which consists of cis-1,1,2,2,3,4-hexafluorocyclobutane and cyclopentane in a weight ratio of 55 to 65/45 to 35 under atmospheric pressure.
8. The azeotropic composition of claim 1, which consists of cis-1,1,2,2,3,4-hexafluorocyclobutane and n-octane in a weight ratio of 95 to 97/5 to 3 under atmospheric pressure.
9. The azeotropic composition of claim 1, which consists of cis-1,1,2,2,3,4-hexafluorocyclobutane and isooctane in a weight ratio of 85 to 89/15 to 11 under atmospheric pressure.
10. The azeotropic composition of claim 1, which consists of cis-1,1,2,2,3,4-hexafluorocyclobutane and n-heptane in a weight ratio of 85 to 90/15 to 10 under atmospheric pressure.
11. The azeotropic composition of claim 1, which consists of cis-1,1,2,2,3,4-hexafluorocyclobutane and methylcyclohexane in a weight ratio of 85 to 91/15 to 9 under atmospheric pressure.
12. The azeotropic composition of claim 1, which consists of cis-1,1,2,2,3,4-hexafluorocyclobutane, ethanol and n-heptane in a weight ratio of 78 to 84/6 to 8/10 to 14 under atmospheric pressure.
13. The azeotropic composition of claim 1, which consists of cis-1,1,2,2,3,4-hexafluorocyclobutane, tert-butanol and n-octane in a weight ratio of 93 to 97/1 to 3/2 to 4 under atmospheric pressure.
14. The azeotropic composition of claim 1, which contains 0.1 to 5% by weight of nitromethane as a stabilizer.
15. A cleaning composition comprising the azeotropic composition of claim 1.

16. A degreasing composition comprising the azeotropic composition of claim 1.

17. A flux removing composition comprising the azeotropic composition of claim 1.

18. A method of cleaning surfaces of solid articles by using the cleaning composition of claim 15.

19. A drying agent composition for dewatering, which comprises the azeotropic composition of any of claims 1 to 6.

20. A method of drying surfaces of solid articles by using the drying agent composition for dewatering of claim 19.

21. A foaming agent comprising the azeotropic composition of claim 1.

22. A method of producing a foamed resin article through expansion by using the foaming agent of claim 21.

23. A method of cleaning surfaces of solid articles by using the cleaning composition of claim 16.

24. A method of cleaning surfaces of solid articles by using the cleaning composition of claim 17.

* * * * *